United States Patent [19]
Crawford

[11] Patent Number: 5,941,817
[45] Date of Patent: Aug. 24, 1999

[54] ENDOSCOPE WHEREIN ELECTRICAL COMPONENTS ARE ELECTRICALLY ISOLATED FROM PATIENT-ENGAGING COMPONENTS

[75] Inventor: John O. Crawford, Hopkinton, Mass.

[73] Assignee: Vista Medical Technologies, Inc., Carlsbad, Calif.

[21] Appl. No.: 08/748,773

[22] Filed: Nov. 14, 1996

[51] Int. Cl.[6] .................................................. A61B 1/04
[52] U.S. Cl. .......................... 600/134; 600/110; 600/109
[58] Field of Search .................... 600/109, 134, 600/110

[56] References Cited

U.S. PATENT DOCUMENTS

| | | | |
|---|---|---|---|
| 4,116,198 | 9/1978 | Roos | 128/303.15 |
| 4,409,993 | 10/1983 | Furihata | 128/784 |
| 4,519,391 | 5/1985 | Murakoshi | 128/303.15 |
| 4,607,621 | 8/1986 | Wheeler | 128/6 |
| 4,652,083 | 3/1987 | Laakmann | 350/96.32 |
| 4,677,471 | 6/1987 | Takamura | 600/110 |
| 4,686,964 | 8/1987 | Yunoki et al. | 128/4 |
| 4,688,893 | 8/1987 | Laakmann | 350/96.32 |
| 4,803,550 | 2/1989 | Yabe et al. | 358/98 |
| 4,823,043 | 4/1989 | Roberts et al. | 313/231.61 |
| 4,879,992 | 11/1989 | Nishigaki | 600/110 |
| 4,917,621 | 4/1990 | Grossi et al. | 439/224 |
| 4,989,586 | 2/1991 | Furukawa | 600/110 |
| 4,993,405 | 2/1991 | Takamura | 600/110 |
| 5,305,736 | 4/1994 | Ito | 600/109 |
| 5,359,453 | 10/1994 | Ning | 600/182 |
| 5,370,108 | 12/1994 | Miura | 600/110 |
| 5,372,587 | 12/1994 | Hammerslag | 604/95 |
| 5,390,662 | 2/1995 | Okada | 128/4 |
| 5,634,881 | 6/1997 | Francis | 600/920 |

Primary Examiner—Gene Mancene
Assistant Examiner—Ira Hatton
Attorney, Agent, or Firm—Pandiscio & Pandiscio

[57] ABSTRACT

An endoscope comprises inner and outer tubes, the inner metal tube containing electrical an objective unit components including a solid state video imaging unit. An electrically insulative sleeve is disposed around the inner tube for electrically isolating the inner tube and electrical components from the outer tube. In a preferred embodiment, an electrically insulative ring is disposed between a major portion of the inner tube and distal end portion of the inner tube to electrically isolate the inner tube distal end portion from the inner tube major portion and the electrical components. Thus, those endoscope components which are likely to contact a patient, i.e., the outer tube and the inner tube distal end portion, are electrically isolated from the inner tube and the electrical components therein, thereby preventing injurious electrical current flow to the patient.

23 Claims, 4 Drawing Sheets

ENDOSCOPE WHEREIN ELECTRICAL COMPONENTS ARE ELECTRICALLY ISOLATED FROM PATIENT-ENGAGING COMPONENTS

BACKGROUND OF THE INVENTION

1. Field of the Invention

This invention relates to endoscopes for use in surgical arts, and is directed more particularly to electronic endoscopes.

2. Description of the Prior Art

Endoscopes, which are instruments used to inspect cavities or openings, have found a great number of applications in medicine and other technologies. In the field of medicine, the use of endoscopes permits inspection of organs, or other biological specimens, for the purpose of inspecting a surgical site, sampling tissue, and/or facilitating the manipulation of other surgical instruments, usually with the objective of avoiding invasive and traumatizing surgical procedures.

Older conventional endoscopes used in medicine have an objective lens unit at their distal (forward) ends which transmits an image of the area forward of the objective lens unit to the proximal (rear) end of the endoscope for viewing in an eye-piece, the image being transmitted to the eye-piece via an image forwarding means in the form of a relay lens set, or an optical fiber bundle unit. In more recent years, in place of the eye-piece and at least part of the image forwarding means, it has been preferred to provide a small size solid state video imaging device, such as one constituting a CCD chip, in the imaging plane of the objective lens, and applying the output of that video imaging device via a suitable electronic transmission system to a video monitor for viewing by a user. With both types of image transmitting and viewing arrangements, a surgeon can view the displayed image and use the information conveyed by that image to manipulate the endoscope and other surgical instruments that have been inserted into the patient via another incision or opening in the patient's body. In the case of endoscopes that incorporate a solid state video imaging device, the image seen by the objective lens unit can be observed in a display provided by the video monitor, with or without magnification.

In U.S. patent application Ser. No. 08/319,886, filed Oct. 7, 1994, in the names of Koichiro Hori, et al., there are shown and described optical, electronic and mechanical components of a contemporary endoscope.

In the case of endoscopes that do not have electronics in the tube which is inserted into the patient, there are minimal problems with current leakage that might adversely affect the patient. However, in the case of endoscopes that have a solid state imaging device and/or other electronic or electrical components embodied in the insertion tube portion of the endoscope, there is the possibility of current leakage. In one form of the electronic endoscope, the insertion portion comprises a dual tube construction, with the solid state imaging device and other electronic or electrical components being mounted in the innermost tube of the dual tube insertion portion. The possibility of a patient-injuring current leakage is particularly grave in the case where an electrified instrument, e.g., an electrified cauterizing instrument, is used in proximity to the endoscope. The possibility of a patient-injuring electrical current flow when using an endoscope is a problem in need of solution.

SUMMARY OF THE INVENTION

A general object of the invention is to provide an endoscope wherein components which contact a patient, i.e., an outer tube and an inner tube distal end portion, are electrically insulated from electrical components in the endoscope.

A more specific object of the invention is to provide an endoscope wherein the outer surface of the insertion portion of the endoscope is electrically isolated from electrical components in the endoscope.

A further more specific object of the invention is to provide an endoscope wherein a patient-engaging inner tube distal end portion of the endoscope is electrically isolated from electrical components in the endoscope.

With the above and other objects in view, as will hereinafter appear, a feature of the present invention is the provision of an endoscope comprising inner and outer tubes, the inner tube housing electrical components therein. An electrically insulative sleeve is disposed on the inner tube for electrically isolating the outer tube from the inner tube and the electrical components therein. Also an electrically insulative means preferably is disposed between a major portion of the inner tube and a distal end portion of said inner tube to electrically isolate the inner tube distal end portion from the inner tube major portion and the electrical components therein.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DESCRIPTION OF THE PREFERRED EMBODIMENT

Figure 1:
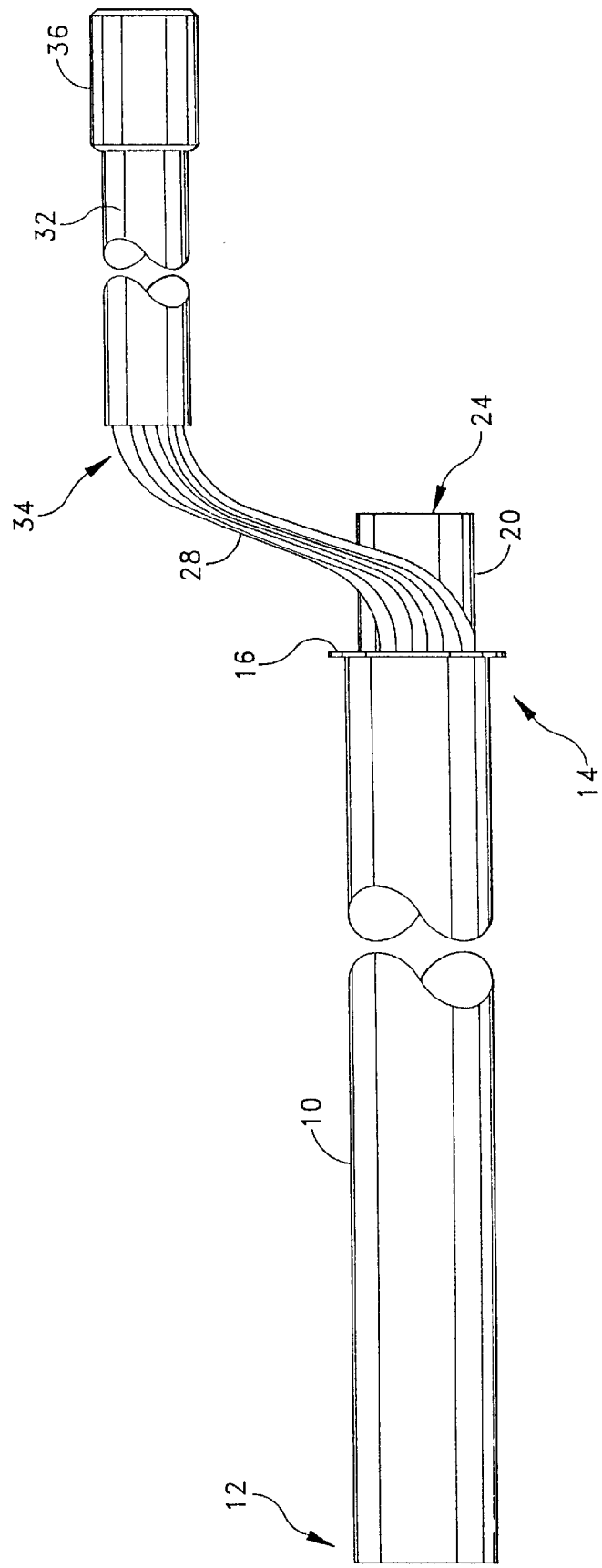
FIG. 1 is a fragmentary elevational view of the insertion portion of an endoscope illustrative of an embodiment of the invention.
Figure 2:
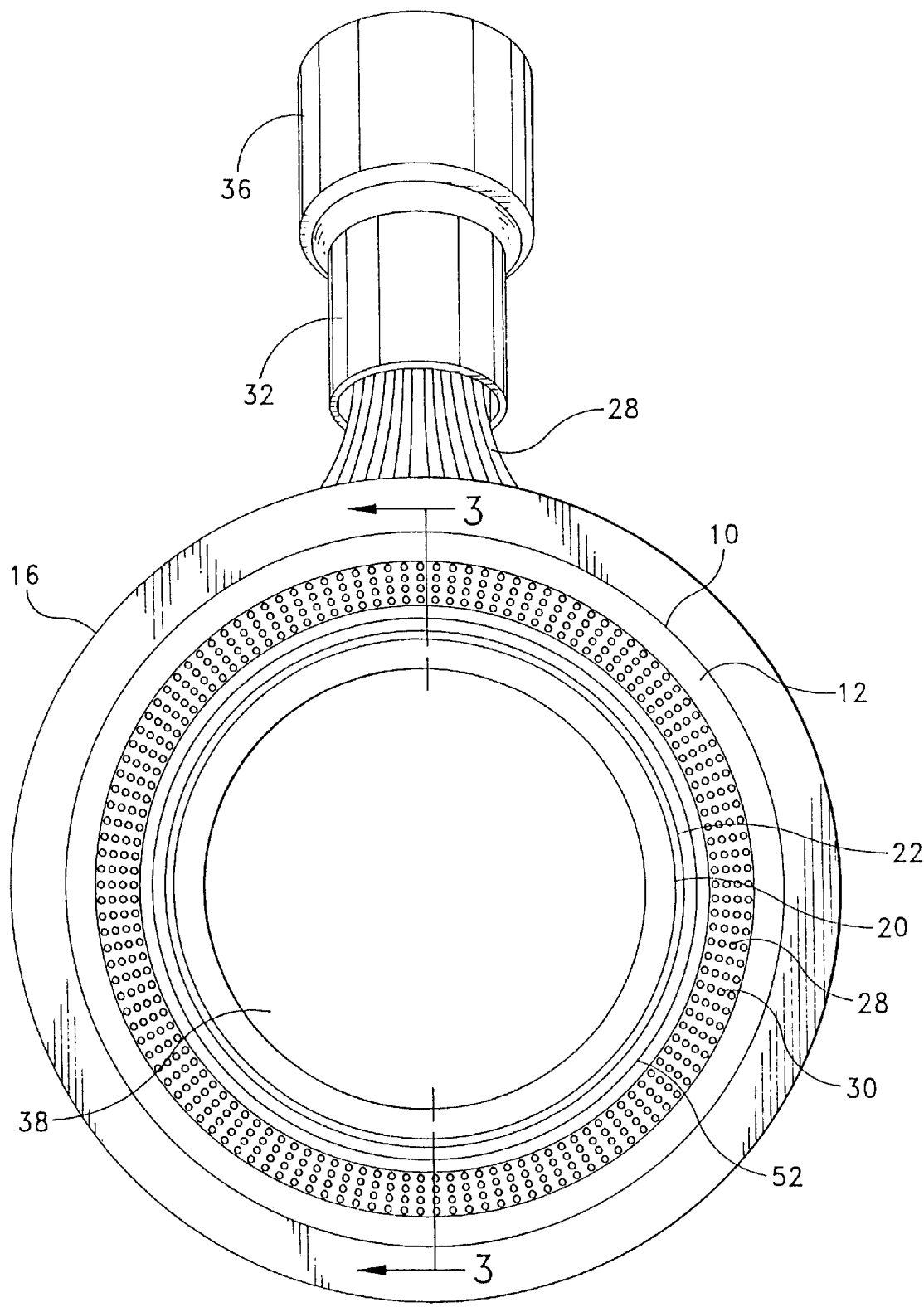
FIG. 2 is a distal end elevational view of the insertion portion shown in FIG. 1.
Figure 3:
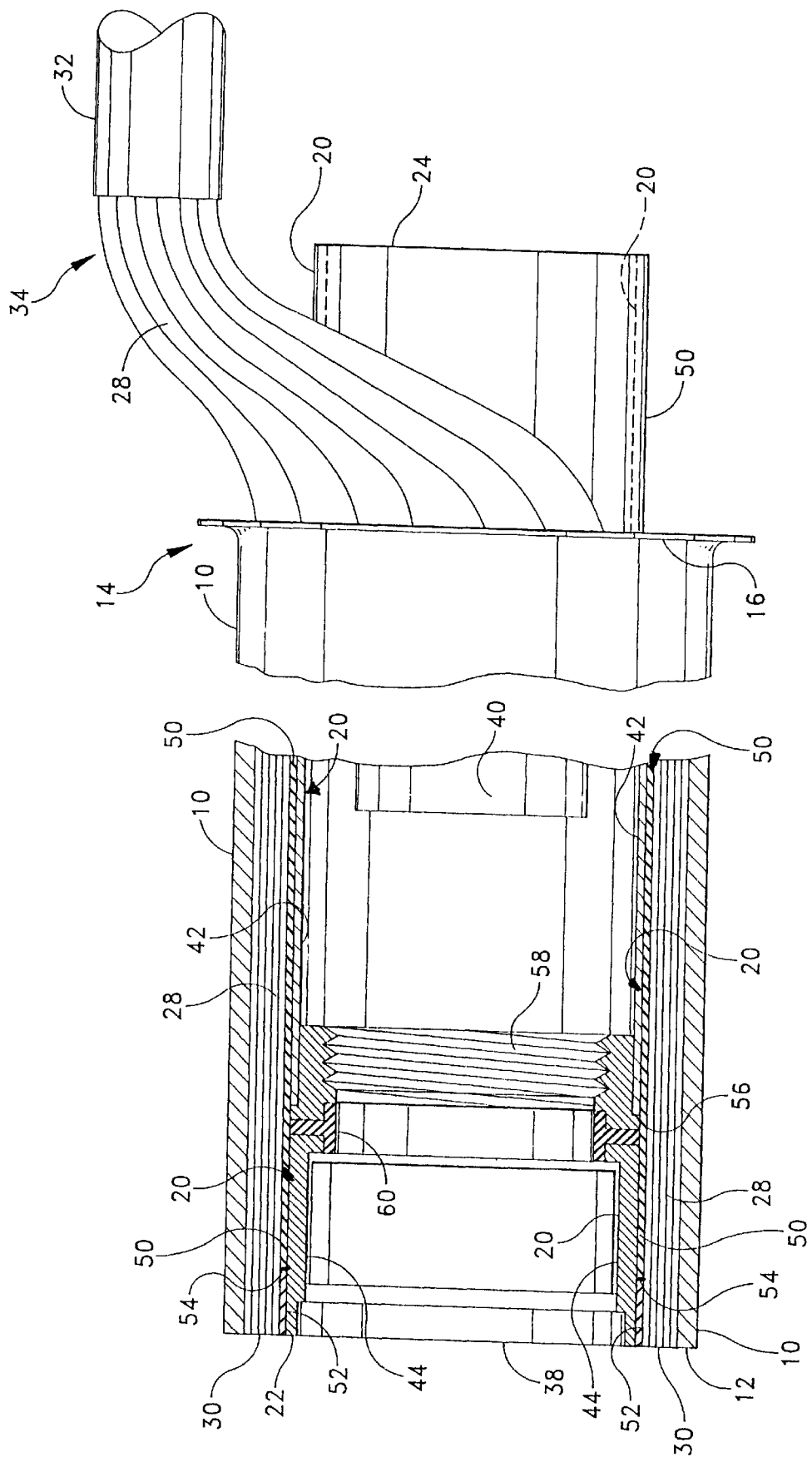
FIG. 3 is a fragmentary sectional view in elevation taken substantially along line 3—3 of FIG. 2.

Referring to FIGS. 1–3, it will be seen that an illustrative embodiment of the invention comprises an endoscope insertion portion 2 that includes a cylindrical outer tube 10 open at a distal end 12 thereof. Typically, a proximal end 14 of the outer tube 10 extends into a suitable support (not shown) in the form of a housing, mounting frame, or handle, such as the one shown and described in U.S. patent applications Ser. Nos. 08/319,886, filed Oct. 7, 1994 by Koichiro Hori et al (Attorney Docket No. OKTA-1) and 08/545,927 filed Oct. 20, 1995, in the name of Koichiro Hori (Attorney Docket No. OKTA-6). The disclosures of those patent applications are incorporated herein by reference.

Mounted within the outer tube 10 is a cylindrical inner tube 20. A distal end 22 of inner tube 20 terminates in substantially the same plane as the distal end 12 of the outer tube 10. A proximal end 24 of the inner tube 20 extends beyond the proximal end 14 of the outer tube 10 and is mounted to the same housing, mounting frame or handle (not shown) as outer tube 10. Although not shown, it is be understood that that tubes 10 and 20 are electrically insulated from one another where they are attached to their support (i.e., the housing, mounting frame or handle, not shown).

The inner tube 20 is smaller in diameter than the outer tube 10 and is mounted in the outer tube 10 so as accommodate a plurality of optical fibers 28 that are used to transmit light to illuminate surgical site in front of the endoscope. At their rear ends fibers 28 project out of the proximal end 14 of the outer tube 10 and are collected in a bundle in a protective sheathing 32, preferably of a flexible electrically-insulating, water-impermeable material such as polyethylene or silicone rubber, thereby forming an optical fiber cable. Preferably the proximal ends 34 of fibers 28 are captured in a ferrule 36 (FIGS. 1 and 2) that serves as a connector for the optic fiber cable whereby that cable can be connected to a suitable light source (not shown). The proximal end 14 of the outer tube 10 may be provided with an entry flange 16 to facilitate connection thereof to the aforementioned support. The inner surface of tube 10 at the junction with flange 16 is preferably curved so as to minimize abrasion or stressing of the optical fibers.

Figure 4:
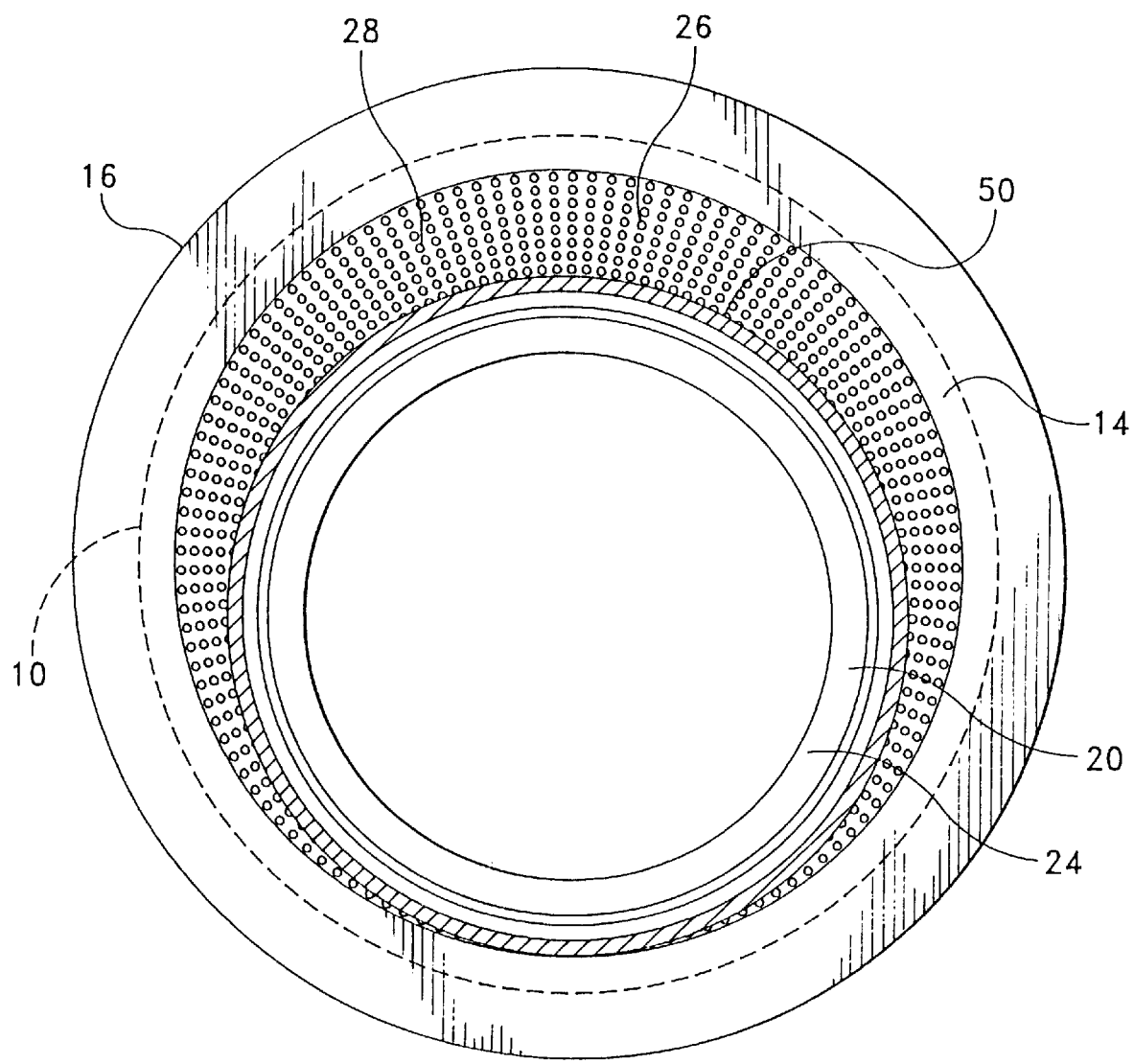
FIG. 4 is a proximal end elevational view of the dual tube insertion portion shown in FIG. 1.

At their rear or proximal ends the two tubes are somewhat eccentric to one another so as leave a crescent shaped area 26 (FIG. 4) to permit the bundle of optical fibers to be spread out to a more generally annular pattern, whereas at the front (distal) ends of tubes 10 and 20 the two tubes are generally cylindrical and the fibers 28 are more or less uniformly distributed about the periphery of the inner tube, as shown in FIG. 2, whereby light is projected forwardly from the distal end of the endoscope in a substantially uniform pattern around the circumference of the dual tube insertion portion, so as to better illuminate a surgical site. The distal ends 30 of the fibers 28 may (but need not) be bonded to one another by a suitable cement, such as an epoxy resin. However, the fibers 28 are locked in place in the gap between the two tubes 10, 20, with their distal ends 30 being optically polished and preferably terminating substantially flush with the plane of the distal end 12 of the outer tube 10, as shown in FIG. 3

Referring to FIG. 3, it will be seen that the inner tube 20 comprising first and second tube sections 42 and 44 that are aligned and disposed proximate each other end-to-end. The first inner tube section 42 comprises an elongated major and proximal portion of the inner tube 20 and the second inner tube section 44 comprises a distal end portion of the inner tube 20. The smaller and distal 22 of the second inner tube section 44 is exposed around the periphery of a window 38 (hereinafter described) and thus is subject to contact with a patient.

Mounted within the distal end 22 of the inner tube section 44 are a transparent window pane 38 and a discrete objective lens unit shown schematically at 46. It is to be noted that window 38 is not essential to the invention and may be omitted, in which case the front surface of the objective lens unit serves as the window. Detail of the objective lens unit are omitted from the drawings since the form of that unit is not critical to the invention. Moreover, the construction and function of such units are well known in the art, as exemplified by U.S. Pat. Nos. 4,488,039; 4,491,865; 4,745,470; 4,745,471; 4,832,003; 4,867,137; and 5,122,650 and the patent applications cited above.

Also mounted within inner tube 20 is a solid state video imaging unit represented schematically at 40. Other electronic means (not shown) associated with the solid state imaging means also may be mounted within inner tube 20. Details of the video imaging unit and associated electronic components are omitted from the drawings since such the form of such units is not critical to the invention and the construction and mode of operation of such units are well known in the art, as exemplified by U.S. Pat. Nos. 4,488,039; 4,491,865; 4,867,139; and 5,166,787 and the patent applications cited above.

An electrically insulative sleeve 50 (FIG. 3) is affixed, as by heat shrinking, on the inner tube 20, covering the whole of the first elongated major section 42 and at least a portion of the second section 44 of the inner tube. The sleeve 50 preferably is made of a high dielectric strength polyester that is capable of shrinking when heated, and has a wall thickness of about 0.001 inch. An electrically insulative fitting, preferably in the form of a ring 52, fills the gap at the distal end 54 of the insulative sleeve 50 between fibers 28 and the distal end of inner tube section 44. The ring 52 preferably is made of a high dielectric strength material, such as a polymerized epoxy resin.

At the distal end 56 of the first elongated major section 42 of the inner tube 20 there may be provided a threaded metal fitting 58 for receipt of an internal component, such as a relay lens (not shown). Disposed between the first and second inner tube sections 42 and 44 may be an electrically insulative fitting 60 which may abut the metal fitting 58, if such is present. Fitting 60 also abuts the inside surface of insulative sleeve 50. Fitting 60 preferably is of a high dielectric strength material so as to electrically isolate the two inner tube sections 42 and 44 from one another. Fittings 58 and 50 form part of the inner tube 20.

The parts of the endoscope which are electrically conductive and which come into contact with the patient, i.e., the distal end section 44 of inner tube 20 and the outer tube 10 are electrically insulated and isolated from the major section 42 of inner tube 20 and the imaging device 40 and other components (not shown) mounted within the inner tube section 42. Thus, if the outer tube 10 and/or the inner tube distal end section 44 should come in contact with an electrically energized tool, e.g. a cauterizing tool or similar device, those insulated elements cannot form parts of a closed electrical circuit that includes inner tube section 42 and the patient. Moreover, if so desired, the inner tube 20 may be grounded, as by being in electrical communication with ground 62 (FIG. 1), which may be video or case ground. Such grounding can aid in noise rejection by the imaging device 40 and its associated circuitry.

There is thus provided an endoscope in which the possibility of excessive and injurious current flow to the patient via the endoscope is avoided.

It is to be understood that the present invention is by no means limited to the particular construction herein disclosed and/or shown in the drawings, but also comprises any modifications or equivalents within the scope of the claims.

What is claimed is:

1. An endoscope having an insertion portion that comprises inner and outer tubes, with outer tube being coextensive with said inner tube and said inner tube housing an objective lens unit and electrical components including a solid state video imaging unit; and an electrically insulative sleeve surrounding said inner tube for electrically isolating said inner tube and said electrical components from said outer tube.

2. An endoscope having an insertion portion that comprises inner and outer electrically conductive tubes, with said inner tube housing electrical components, said inner tube comprising first and second electrically conductive sections in end to end relation, and means for electrically isolating said first section from said second section.

3. An endoscope according to claim 2 wherein said means for electrically isolating said first section from said second section comprises an electrically insulative ring disposed between said first and second sections of said inner tube.

4. An endoscope in accordance with claim 1 wherein said sleeve is made of a plastic material and is heat shrunken onto said inner tube.

5. An endoscope in accordance with claim 1 wherein said sleeve is of high dielectric strength material.

6. An endoscope in accordance with claim 5 wherein said high dielectric strength material is a polyester.

7. An endoscope in accordance with claim 1 wherein said inner and outer tubes define therebetween an annular gap, and fiber optic strands are disposed in said gap between said sleeve and said outer tube.

8. An endoscope in accordance with claim 1 further including means for electrically grounding said inner tube.

9. An endoscope comprising:
   an elongate electrically conductive inner tube;
   an objective lens unit and a solid state video imaging unit mounted within said inner tube;
   an electrically insulative sleeve surrounding and covering an outer surface of said inner tube; and
   an elongate electrically conductive outer tube disposed around said inner tube and electrically insulated from said inner tube by said sleeve, said outer tube being coextensive with said inner tube.

10. An endoscope in accordance with claim 9 wherein said sleeve is of high dielectric strength material.

11. An endoscope in accordance with claim 10 wherein said sleeve is made of a plastic material and is heat shrunken onto said elongate inner tube.

12. An endoscope in accordance with claim 9 wherein said inner and outer tubes define therebetween an annular gap, and fiber optic strands are disposed in said gap.

13. An endoscope in accordance with claim 9 wherein said sleeve covers substantially the whole outer surface of said inner tube.

14. An endoscope in accordance with claim 9 wherein said elongated inner tube is electrically grounded.

15. An endoscope comprising:
   An elongated first inner tube section housing electrical components;
   a second inner tube section in alignment with said elongated first inner tube section and disposed proximate a distal end of said elongated first inner tube section;
   an electrically insulative sleeve surrounding said elongated first inner tube section along the entire length of said first inner tube section and also surrounding said second inner tube along a portion of the length thereof adjacent said first inner tube section;
   an electrically insulative fitting disposed between said distal end of said elongated first inner tube section and a proximal end of said second inner tube section, said fitting abutting an inner surface of said sleeve; and
   an outer tube surrounding said first and second inner tube sections, said sleeve and said fitting, whereby said outer tube is electrically isolated from said first and second inner tube sections and said electrical components.

16. The endoscope in accordance with claim 15 wherein said sleeve is made of a high dielectric strength polyester.

17. An endoscope in accordance with claim 15 wherein said first inner tube section is electrically grounded.

18. An endoscope characterized by an insertion portion that has a distal end and a proximal end and comprises inner and outer electrically conductive tubes with a gap between said tubes, said outer tube being coextensive with said inner tube;
   at least one objective unit and at least one solid state imaging device mounted within said inner tube, with said at least one objective unit in position to view an object located in front of said distal end of said insertion portion;
   a plurality of optical fibers disposed in said gap for use in conducting light to illuminate said region; and
   an electrically insulative sleeve surrounding said inner tube for electrically isolating said inner tube and said electrical components from said outer tube, said electrically-insulative sleeve being located between said inner tube and said optical fibers and extending for the full length of said inner tube.

19. The endoscope in accordance with claim 18 wherein said sleeve is made of a high dielectric strength plastic material.

20. An endoscope in accordance with claim 18 further including electrically insulative means disposed between a major portion of said inner tube and a distal end portion of said inner tube to electrically isolate said inner tube distal end portion from said inner tube major portion, and further wherein said at least one solid state imaging device is located within said major portion of said inner tube.

21. An endoscope in accordance with claim 19 wherein said sleeve is heat shrunken onto said inner tube.

22. An endoscope in accordance with claim 19 wherein said inner tube is electrically grounded.

23. An endoscope in accordance with claim 12 wherein fiber optic strands are disposed in surrounding relation to said sleeve.

* * * * *

UNITED STATES PATENT AND TRADEMARK OFFICE
CERTIFICATE OF CORRECTION

PATENT NO.    :   5941817
DATED         :   August 24, 1999
INVENTOR(S)   :   John O. Crawford It is certified that error appears in the above-indentified patent and that said Letters Patent is hereby corrected as shown below:

Claim 1, Column 4, Line 59, insert the word "said" before the word -- outer -- (second occurrence).

Signed and Sealed this

Twenty-ninth Day of February, 2000

Attest:

Q. TODD DICKINSON

Attesting Officer

Commissioner of Patents and Trademarks